United States Patent [19]

Johnson

[11] Patent Number: 4,670,012
[45] Date of Patent: Jun. 2, 1987

[54] DIAPER OR INCONTINENT PAD HAVING PLEATED ATTACHMENT STRAP

[75] Inventor: Nordahl K. Johnson, Puyallup, Wash.

[73] Assignee: Weyerhaeuser Company, Tacoma, Wash.

[21] Appl. No.: 755,126

[22] Filed: Jul. 15, 1985

[51] Int. Cl.⁴ ............................................. A41B 13/02
[52] U.S. Cl. .................................... 604/390; 604/389
[58] Field of Search ............... 604/390, 391, 392, 386, 604/389, 385, 393, 394

[56] References Cited

U.S. PATENT DOCUMENTS

| | | | |
|---|---|---|---|
| 3,776,234 | 12/1973 | Hoey | 128/287 |
| 3,901,239 | 8/1975 | Tritsch | 128/287 |
| 3,930,502 | 1/1976 | Tritsch | 604/390 |
| 3,952,744 | 4/1976 | Aldinger | 128/287 |
| 3,999,544 | 12/1976 | Feldman et al. | 128/284 |
| 4,014,399 | 3/1977 | Tritsch | 128/287 |
| 4,060,085 | 11/1977 | Karami | 128/287 |
| 4,127,132 | 11/1978 | Karami | 604/390 |
| 4,317,449 | 3/1982 | Nowakoski | 128/287 |
| 4,578,072 | 3/1986 | Lancaster | 604/390 |

FOREIGN PATENT DOCUMENTS 2418209 10/1975 Fed. Rep. of Germany ...... 604/390

*Primary Examiner*—C. Fred Rosenbaum
*Assistant Examiner*—John D. Ferros

[57] ABSTRACT

The invention is an improved attachment strap for a large diaper or adult incontinent pad. It consists of an accordion pleated length of material, preferably a nonwoven fabric, with one end permanently attached to the diaper body. The final pleat at the opposite end is terminated by a length of peelable pressure sensitive tape which overhangs each edge of the pleat. The medially oriented overhang is relatively narrow while the laterally oriented overhang, which ultimately serves as an attachment tab, is relatively wider. When in stored position, the two overhanging portions hold the folded tape compactly against the back face of the diaper where they do not interfere with manufacturing or packaging operations. The peelable attachment tape has an adhesive coating that is relatively high in shear strength but modest in peel strength. These characteristics are chosen so that the tape can be peeled off without tearing the diaper backing sheet. The diaper can be removed for inspection and then be reused, if unsoiled, without damage to the backing sheet.

9 Claims, 10 Drawing Figures

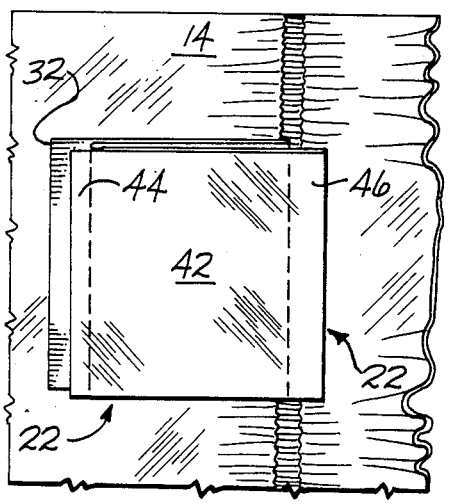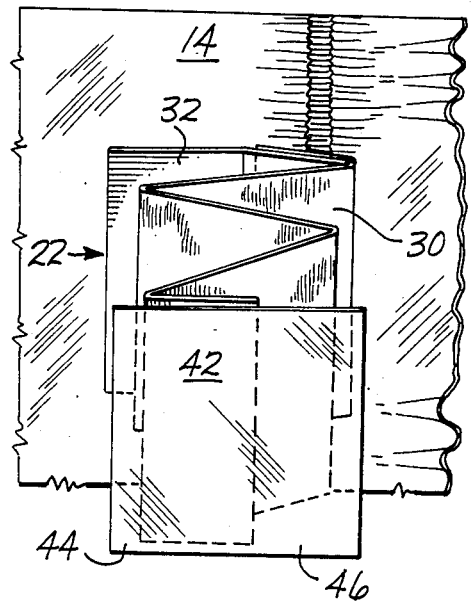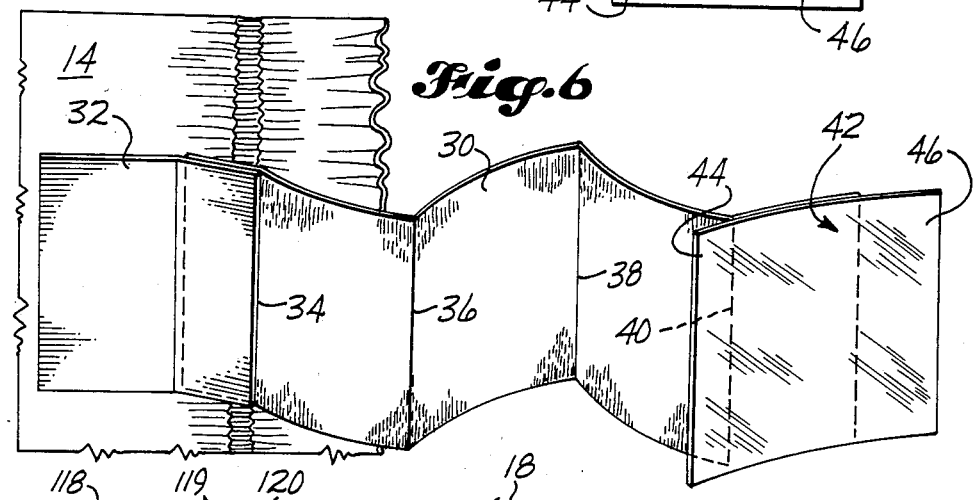
Fig. 7 PRIOR ART
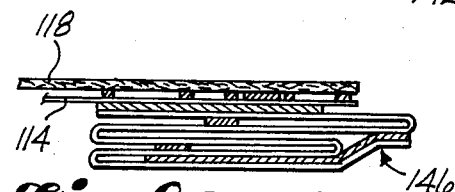
Fig. 8 PRIOR ART
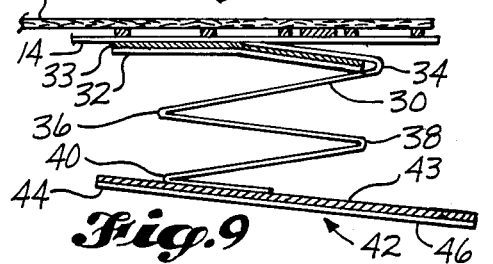
Fig. 9
Fig. 10

DIAPER OR INCONTINENT PAD HAVING PLEATED ATTACHMENT STRAP

BACKGROUND OF THE INVENTION

The present invention relates to a disposable diaper or incontinent pad having a pleated attachment strap which is inexpensive and easily manufactured and which offers improved comfort to the wearer.

Disposable diapers for infant and toddler use have been generally available for approximately two decades. Typical products of this type are described in U.S. Pat. Nos. 3,612,055 to Mesek, et al. and Re. 26,151 to Duncan. Innumerable improvements have been made over the years to these rather basic designs. One of the more useful improvements has been the development of adhesively coated tape systems to replace pins or other fasteners for holding the diaper in place on a baby. A large body of patent literature has developed dedicated exclusively to improvements in attachment tapes. The interested reader will find a good historical review of this technology in U.S. Pat. No. 4,014,339 to Tritsch.

Early manufacturers of diapers using tape closure systems faced a number of technical problems. Initially the tape closures projected from the marginal edges of the diapers. These projecting tapes caused serious problems during manufacturing. Torn diaper covers and missing tapes were a frequent occurrence due to snagging on conveyor lines and packaging equipment. A relatively early patent to Hoey, U.S. Pat. No. 3,776,234, describes an attachment tape folded inwardly to prevent interference with manufacturing equipment. Nonprojecting tapes soon became quite standard as methods were developed by other inventors to retain them entirely within the rectangular outline of the diaper until the time of use. At the same time, methods were developed to hold the tape closures flat against the body of the diaper in order to further minimize the risk of snagging. Tritsch, in U.S. Pat. No. 3,930,502, shows a tape folded in "S" fashion. Aldinger, U.S. Pat. No. 3,952,744, shows a folded tape with one end of a strippable release paper attached to the diaper back in order to hold the tape flat and in a noninterfering position during further manufacturing steps. Similar arrangements are also shown in U.S. Pats. Nos. 3,901,239 to Tritsch; 3,999,544 to Feldman, et al.; and 4,060,085 to Karami.

It has only been in the last several years that disposable diapers have been available in larger sizes for use by incontinent adults. The design of these adult products has been much more complex than making a simple scale-up of diapers originally designed for infants. For one thing, the body sizes of the wearers vary greatly. A product which might be inadequately small for one person may be unacceptably sloppy when worn by another individual. As with products designed for infants, a tight, snug fit is essential if leakage is to be prevented. For this reason, adult products are normally available in several sizes. This problem has further complicated the use of closure tabs. Nowakoski, in U.S. Pat. No. 4,317,449, shows a Z-shaped tab which expands to form a short strap. The inventor notes that these tapes may be as long as 17.5 cm (7 in.) and comments that tapes of this length have never before been used on a disposable diaper product. Judging from the patent drawings, the Nowakoski incontinent pad is an extremely wide product which is designed to completely encircle the hip area of the wearer. Products of this type have not generally been found to be acceptable because they tend to bunch up very badly in the crotch area and are both uncomfortable and prone to leakage. More recent products are much narrower so that they resemble a loincloth with the hip area remaining uncovered. These products have required much longer closure straps than those described by Nowakoski with the lengths generally varying from about 18–46 cm (7–18 in.). These tapes generally encircle the waist area of the wearer and act in the manner of a belt.

While the open-sided adult incontinent pads have greatly increased the comfort to the wearer and reduced the chances of leakage, the necessary longer attachment tapes have proved to be a manufacturing nightmare. No longer can they be formed into a simple Z-fold as was done by Nowakoski. One commercially available product is made with the tapes accordion pleated with spots of an adhesive having a low bonding strength placed between each of the pleats to prevent them from springing apart during manufacture. Making a product of this type is complex and expensive and an improved design for these tapes has been a long-sought goal.

The present invention is a major step forward in the design of long attachment tapes or straps for use with adult incontinent products.

SUMMARY OF THE INVENTION

The present invention is a disposable diaper or incontinent pad especially adapted for adult use. In particular, it is an improved method of forming and retaining the attachment straps during manufacture and prior to the time of use.

The diaper or pad itself is entirely conventional. It will have a moisture pervious body contacting facing sheet, usually made of a nonwoven material, and a moisture impervious backing sheet, generally coextensive with the facing sheet. An absorbent pad or panel, usually of fluffed wood pulp, is disposed between the backing and facing sheets.

A pair of the improved fasteners of the present invention are located on opposite edges at one end of the diaper near adjacent corners. Each of these fasteners comprises a flexible attachment strap which is accordion pleated to form a folded unit having a plurality of generally coextensive articulated segments. The initial segment at the proximal end of the attachment strap is permanently anchored to the backing sheet, preferably by adhesively bonding it or by the use of a strip of pressure sensitive adhesive tape having a permanent type adhesive. The final segment at the opposite or distal end of the attachment strap is terminated by a pressure sensitive adhesive backed tape having a repositionable-type adhesive. This repositionable adhesive backed tape is sized so as to overhang each edge of the final segment and the associated coextensive pleated strap unit. The overhanging portions serve to hold the entire unit compactly against the diaper backing sheet until the time of use. At that time, the adhesive backed tape can be peeled from the backing sheet while remaining attached to the strap. The strap can then be extended and one of the overhanging portions of the adhesive backed tape serves as an attachment tab to secure the diaper or incontinent pad to the wearer. The repositionable adhesive is preferably one having a relatively low peel strength and high shear strength. Adhesives having these characteristics for use on diaper attachment tapes are now readily available items of commerce.

The flexible attachment strap may be made conventionally of a polyolefin film. However, it is preferred that this strap be made of a nonwoven fabric. The nonwoven product is superior because of its breathability and reduced tendency to cause chafing.

It is an object of the present invention to provide an improved elongated attachment strap for an adult diaper or incontinent pad.

It is a further object to provide an attachment strap which is readily and simply manufactured using a minimum of adhesive coated surfaces.

It is another object to provide an attachment strap for an incontinent pad which may be compactly folded and adhered to the pad in a noninterfering position during manufacturing and packaging steps.

These and many other objects will become readily apparent to those skilled in the art upon reading the following detailed description taken in conjunction with the drawings.

BRIEF DESCRIPTION OF THE DRAWINGS

FIG. 4 is a detailed plan view of an attachment strap as it would be configured during manufacture and shipping.

FIGS. 5 and 6 show the attachment strap being released and extended for use.

FIGS. 7 and 8 are cross-sectional views of a prior art attachment strap in partially released and stored positions, respectively.

FIGS. 9 and 10 are cross-sectional views of the present attachment strap in partially released and stored positions, wherein FIG. 10 is shown as a section along the line 10—10 of FIG. 1.

DESCRIPTION OF THE PREFERRED EMBODIMENTS.

Figure 3:
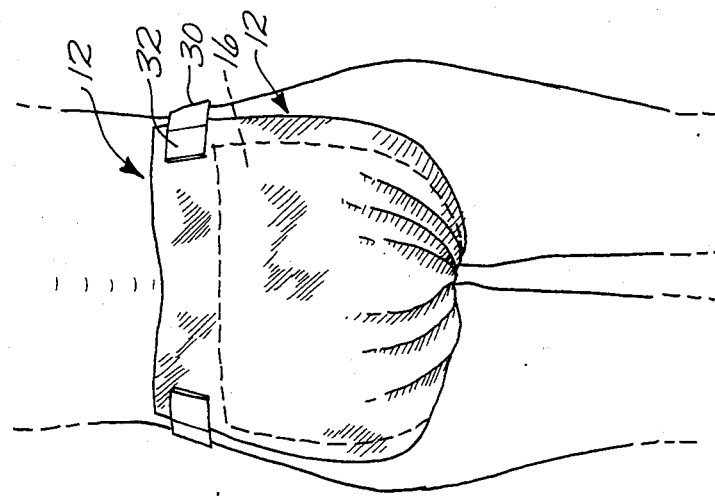
FIG. 3 is a dorsal view as above.
Figure 2:
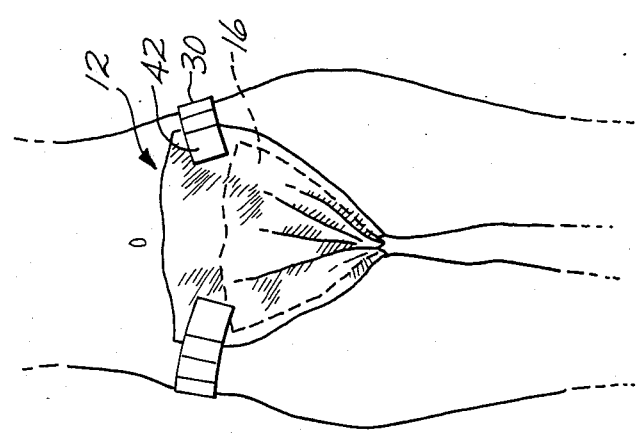
FIG. 2 is a ventral view of the pad in place on a wearer.
Figure 1:
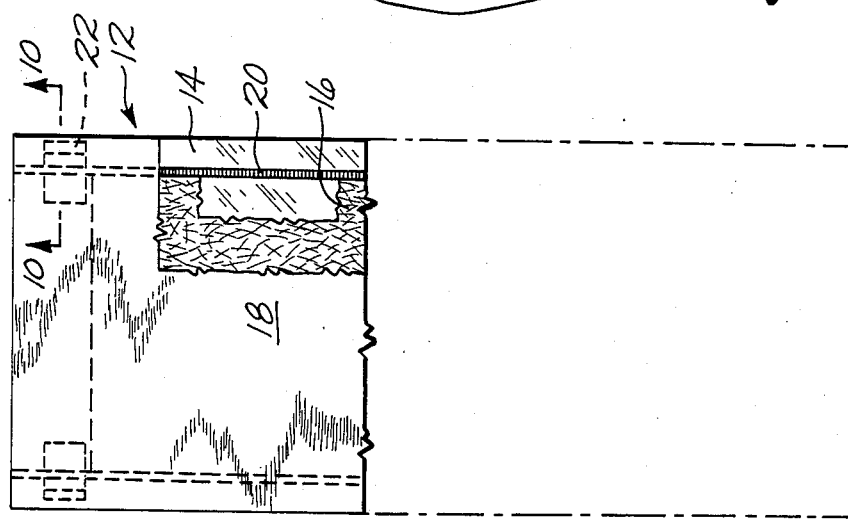
FIG. 1 is a plan view of an adult incontinent pad, partially cut away, looking at the body contacting surface.

Referring to the drawings, FIG. 1 shows an adult diaper or incontinent pad, generally indicated at 12, comprising a polyolefin backing sheet 14, a fluffed wood pulp filler 16, and a moisture permeable nonwoven cover sheet 18. Elastic strips 20 run the full length of the lateral margins of the product and serve to give a tight, leak resistant fit against the body of the wearer. The cover sheet, backing sheet and elastic are secured along the marginal areas by adhesive beads 19 (FIG. 10). A pair of folded attachment straps 22 are located at the lateral edges near adjacent corner regions of the product.

Reference should now be made to FIGS. 4-6, 9 and 10 for a detailed description of the construction of the new attachment strap. Each strap unit 22 is comprised of two or three individual pieces. Principal among these is strap or tape 30 which is preferably a soft, nonwoven material. In the representations shown, this is permanently attached to diaper backing 14 by a pressure sensitive tape 32 having a relatively aggresive adhesive layer 33. Normally it would not be possible to remove tape 32 without tearing backing film 14. Alternatively, strap 30 may be adhesively bonded to backing film 14 or otherwise affixed by means of which thermal bonding would be one example. Tape 30 is folded into a series of accordion pleats by folds 34, 36, 38, and 40. These will typically by of equal width except for the initial and final fold. The number of folds made will be dependent upon the length of the strap. The final fold at the distal end of the strap is affixed to a second tape member 42. This tape is positioned so as to have a short overhanging portion 44 and a longer overhanging portion 46. The adhesive on this tape is chosen so as to be considerably less aggresive to diaper backing sheet 14. Adhesives are now available that exhibit relatively high strength in shear but lower strength in peel. By choosing these characteristics, a diaper can be applied and later removed without tearing the backing sheet. If the diaper is not soiled, it can then be reapplied without any damage having occurred.

Referring particularly to FIGS. 9 and 10, it will become immediately apparent how the tape unit is applied and compactly stored during the balance of any manufacturing and packaging operations. The accordion folded strap 30 is held in place against the diaper backing by the overhanging ends 44, 46 of tape unit 42. End portion 44 can either bear against the nonadhesive surface of tape 32 or against the diaper backing 14. End 46 will normally bear against the diaper backing. For use, these end portions are peeled away from the surface to which they are adhered while remaining attached to the final fold of strap 30. End 46 then becomes the adhesive surface which serves to hold the diaper in place when in use.

The extreme end of portion 46 of tape 42, near the numeral 46 on FIGS. 9 and 10, may optionally be backfolded a short distance to provide a convenient pull tab for ease of removal. For the same reason, the end may be configured to project a short distance from the edge of the diaper, as seen best in FIG. 10.

The simplicity of the present construction can be seen when compared with any of the prior art arrangements designed for coping with long attachment straps. One of these is shown in FIGS. 7 and 8. Here the diaper facing 118, at the marginal edge of a diaper or incontinent pad, is bonded to the moisture impervious backing film 114 by hot melt adhesive beads 119. Elastic ribbon 120 is adhesively held in place. A strap 113 is made of polyethylene film approximately 0.1 mm in thickness by 38 mm wide and of appropriate length. Strap 130 is bonded to diaper backing 114 by and extrusion coated adhesive layer 131. The strap is accordion pleated by folds 134, 136, 138, and 140. Attachment end 142 is coated with a relatively nonaggresive adhesive 143 which may be peeled off and reattached without damaging backing film 114. A portion of the terminal end of adhesive film 143 bears against the first fold area 134 of strap 130 at 146. In order to maintain the other end of the strap bundle intact, it is necessary to use beads of adhesive 148, 150 which are applied to each fold. In order to achieve reliable bonding, it has been found necessary to treat areas 149, 151, and 153 of strap 130 by corona discharge in order to achieve reliable bonding when the tape unit is compressed as shown in FIG. 8. Not only is a tape of this type difficult and expensive to manufacture, but it has been found to be very uncomfortable to a wearer and is frequently a cause of chafing.

Example

A "medium" size adult incontinent pad was made as follows, according to the present invention. The overall dimensions of the pad were 762 mm in length by 330 mm side (30×13 in). A polyethylene backing sheet was made from film 0.32 mm (0.00125 in) in thickness, used with an acrylic bonded nonwoven face sheet having a grammage of 26.8 g/m². This enclosed a pad of fluffed bleached wood pulp fiber weighing 100 g and having outside dimensions of 610×241 mm, but cut out in the central (crotch) portion to a width of 152 mm. The edges of the envelope held elastic strips 6.4 mm wide by 0.18 mm thick, measured in relaxed condition.

Attachment straps were either 50.8 or 76.2 mm in width and of variable length but typically about 355 mm. These were made of Cerex 148F-23 nonwoven fabric having a grammage of 28.8 g/m². Cerex is a registered trademark of Monsanto Corp., St. Louis, Ill. Straps were folded into five pleats; the first or proximal pleat was 42 mm long, followed by 3 pleats each 67 mm in length, and terminated by a distal end pleat 44 mm long. The proximal pleat was bonded to the pad backing sheet by a square of a pressure sensitive tape 75 mm wide by 82 mm long. This tape had an aggressive adhesive which could not be peeled from the backing film without tearing it. The distal pleat was entirely covered by a portion of peelable tape 102 mm long by 75 mm wide. The distal tape had a medial portion overhanging the final fold and the pleated tape unit by about 9 mm. In the installed, folded position this medial portion engaged the surface of the proximal attachment tape. The laterally oriented end of the peelable tape had a length of exposed adhesive 35 mm long and was terminated by a backfolded tab 7 mm long. This portion of the tape serves as the attachment face for holding the strap and pad in place on a wearer. In folded position it bears agains the backing sheet.

Other strap lengths can readily be accommodated by changing either the number or length of the individual folds. However, an odd number of folds should be used so that the initial and final segments of the strap are properly oriented.

Suitable peelable tapes are available from Findley Adhesives, Inc., Elm Grove, Wis. and from other manufacturers. These tapes should have a 90° peel strength from polyethylene within a range of about 224–300 N/m and a 180° peel strength of about 385–494 N/m.

It will be evident to those skilled in the art that many variations would be possible in the design shown without departing from the spirit of the invention. It is the intention of the inventor that his protection be limited only as it is defined in the following claims.

I claim:
1. A disposable diaper or incontinent pad having a body contacting facing sheet, a moisture impervious backing sheet generally coextensive with the facing sheet, an absorbent panel disposed between the backing and facing sheets, and a pair of fastener means located on opposite edges near adjacent corners of the diaper or pad, each of which comprises:
   a flexible attachment strap accordion pleated to form a folded unit comprising a plurality of generally coextensive articulated segments,
   the initial segment of one end of said attachment strap being permanently anchored to the backing sheet,
   the final segment at the opposite end of the attachment strap being terminated by a pressure sensitive adhesive backed tape having a repositionable-type adhesive,
   said repositionable adhesive backed tape overhanging each edge of said final segment and the associated coextensive pleated strap unit whereby the overhanging portions serve to hold said unit compactly against the diaper backing sheet until the time of use, whereupon the adhesive backed tape can be peeled from said backing sheet while remaining attached to the strap so that the strap can be extended and one of the overhanging portions of said adhesive backed tape serve as an attachment tab to secure the strap to the front of the diaper or incontinent pad for use by a wearer.
2. The diaper or incontinent pad of claim 1 in which the initial segment of the attachment strap is adhesively bonded to the backing sheet.
3. The diaper or incontinent pad of claim 2 in which the flexible attachment strap is a nonwoven fabric.
4. The diaper or incontinent pad of claim 2 in which the flexible attahcment strap is a polyolefin film.
5. The diaper or incontinent pad of claim 1 in which the initial segment of the attachment strap is bonded to the backing sheet by a strip of pressure sensitive adhesive tape having a permanent type adhesive.
6. The diaper of incontinent pad of claim 5 in which the flexible attachment strap is a nonwoven fabric.
7. The diaper of incontinent pad of claim 5 in which the flexible attachment strap is a polyolefin film.
8. The diaper or incontinent pad of claim 1 in which the flexible attachment strap is a nonwoven fabric.
9. The diaper or incontinent pad of claim 1 in which the flexible attachment strap is a polyolefin film.

* * * * *